US010481170B2

United States Patent
Du et al.

(10) Patent No.: US 10,481,170 B2

(45) Date of Patent: Nov. 19, 2019

(54) TEST TUBE RACK OF ANALYZER PIPELINE, SHIFT DETECTION METHOD AND DEVICE USING THE SAME

(71) Applicant: SHENZHEN MINDRAY BIO-MEDICAL ELECTRONICS CO., LTD., Shenzhen (CN)

(72) Inventors: Xiansuan Du, Shenzhen (CN); Lijian Hu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 30 days.

(21) Appl. No.: 15/198,436

(22) Filed: Jun. 30, 2016

(65) Prior Publication Data

US 2016/0327585 A1 Nov. 10, 2016
US 2018/0136245 A9 May 17, 2018

Related U.S. Application Data

(63) Continuation of application No. PCT/CN2014/074262, filed on Mar. 28, 2014.

(30) Foreign Application Priority Data

Dec. 31, 2013 (CN) .......................... 2013 1 0754647

(51) Int. Cl.

| | |
|---|---|
| ***G01N 35/02*** | (2006.01) |
| ***G01N 35/00*** | (2006.01) |
| ***B01L 9/06*** | (2006.01) |
| ***A61B 8/08*** | (2006.01) |

(Continued)

(52) U.S. Cl.

CPC ......... *G01N 35/021* (2013.01); *A61B 8/0825* (2013.01); *A61B 8/4461* (2013.01); *A61B 8/5269* (2013.01); *B01L 9/06* (2013.01); *G01N 35/00594* (2013.01); *A61B 8/4427* (2013.01); *G01N 2035/0413* (2013.01)

(58) Field of Classification Search

CPC ............ G01N 35/021; G01N 35/00594; A61B 8/0825; A61B 8/13; A61B 8/14; A61B 8/4245; A61B 8/4461; A61B 8/5269

USPC .......................................................... 422/562

See application file for complete search history.

(56) References Cited

U.S. PATENT DOCUMENTS 8,028,843 B2 * 10/2011 Guzman .................. B01L 9/06 211/85.18

2004/0208787 A1 * 10/2004 Takahashi ............. G01N 35/02 422/64

(Continued)

FOREIGN PATENT DOCUMENTS

| | | |
|---|---|---|
| CN | 1932514 A | 3/2007 |
| CN | 102486824 A | 6/2012 |
| CN | 102527458 A | 7/2012 |

(Continued)

*Primary Examiner* — Benjamin R Whatley

(74) *Attorney, Agent, or Firm* — Kory D. Christensen

(57) ABSTRACT

A test tube rack of an analyzer pipeline includes multiple test tube holders for holding test tubes. The test tube rack of an analyzer pipeline comprises a light blocker configured at a side wall of the test tube rack and across multiple test tube holders. A second feature area is on the light blocker between two adjacent test tube holders, a first feature area is between two adjacent second feature areas and a step gap with a predetermined depth is between the first feature area and a second feature area.

10 Claims, 6 Drawing Sheets

301
300
302
303
305
304

(51) Int. Cl.
*A61B 8/00* (2006.01)
*G01N 35/04* (2006.01)

(56) References Cited

U.S. PATENT DOCUMENTS

2010/0292829 A1* 11/2010 Guzman .................. B01L 9/06
700/213
2013/0130369 A1* 5/2013 Wilson ................. B01L 3/5085
435/289.1

FOREIGN PATENT DOCUMENTS

EP 1326077 A2 7/2003
WO 2009064748 A1 5/2009

* cited by examiner

TEST TUBE RACK OF ANALYZER PIPELINE, SHIFT DETECTION METHOD AND DEVICE USING THE SAME

TECHNICAL FIELD

The present disclosure relates to a test tube rack of an analyzer pipeline, especially relating to an analyzer pipeline system, a test tube rack thereof, a shift detection method and a device using the same.

BACKGROUND

On a pipeline of a blood cell analyzer, a test tube rack carrying test tubes (with blood samples) is transported from a loading platform to a detecting area of the blood cell analyzer by a transporting belt along a track. The test tube rack is shifted one step each time so that each test tube carried on the test tube rack is passed through a test tube detector and a sample needle one by one to let the analyzer detect the reference code of the test tube and conduct sample collections. The distance of one shift step is defined as the width of one test tube unit. For certain reasons, such as lost steps of a stepper motor, the test tube rack may shift to a wrong position (the test tube fails to move to a predetermined position), which would cause wrong reference codes to be detected by the test tube detector and wrong samples to be sampled by the sample needle, so as to make test results fail to match the right sample provider (patient). Obviously, such mis-operations would cause many risks in clinical settings.

To avoid the mentioned clinical risks, an operation for testing whether the test tube rack is shifted to the right position in the pipeline should be conducted. A warning is raised when the test tube rack is shifted to the wrong position. In the conventional method, by distinguishing the differences of reflected signals from different areas, an optical detector is used to detect a feature area on the back side of the test tube rack to implement the above position detection.

Referring to FIG. 1, a middle portion between two test tube holders of the back side of test tube rack 101 is processed to form a groove with a 6 mm depth. The test tube rack 101 is formed as a through hole with a rectangular shape front to back at the location of the test tube holder of the test tube rack 101. A narrower edge 103 is defined between a groove 104 and a rectangular hole 105. The optical detector aims the center of the groove 104 by adjusting positions. The test tube rack 101 is shifted a width of the test tube holder one time then the optical detector is directed to aim at the next groove from the currently aimed groove. In this process, the optical detector detects five feature areas; they are a first groove, a first edge, a test tube, a second edge and a second groove respectively (the test tube is detected since it is located at the rectangular hole of the rack). Because the distance between the groove or the test tube and the optical detector is far, the reflected light from the groove or the test tube to the optical coupler is weak. The reflected light from the edge to the sensor is strong since the distance between the edge and the optical coupler is close. Therefore, the feature of the reflected signal shown in the shifting process would be presented as low—high—low—high—low.

In general, an absolute value determination method is applied in the above signal detection. In the absolute value determination method, a threshold voltage is marked between a groove signal and an edge signal at first, and each voltage signal generated in the sifting process of the test tube rack is used to compare with the threshold voltage. If two voltage signals with an impulse higher than the threshold voltage are detected, it means two edges of the rack have passed through. In other words, the above result proves the rack has shifted to the right position. However, since the detection areas of the sensor include the test tube, the reflected signals reflected in certain angles from a glass test tube with a sample inside could be over the threshold value to generate a false impulse if a tag is not pasted on the test tube. Even when a tag is pasted on the test tube, the surface of some specific tag types may be too bright and cause the reflected signals from the tag that are still too strong to generate a false impulse. Therefore, multiple impulses higher than the threshold voltage may be detected between two grooves so as to cause a false negative determination even when the test tube rack is shifted to the wrong position. Under the above, conventional skills for detecting the shift state of the test tube rack are not reliable; it still contains chances for wrong or missing detections, so the clinical risk still exists.

In addition, for figuring out clinical issues, such as temperature variances, sensor aging, and errors of the track (the track has a certain width; a 1 mm tolerance should be defined under the above width) causing the value of reflected signals floating over the threshold voltage to affect the viability of the detecting result, a high-performance sensor/optical detector is the only choice to implement the above conventional solution since only the optical detector has enough sensitivity to satisfy the high demand of the above solution. The purpose for applying the optical detector is to enlarge the differences between the groove signal and the edge signal as much as possible. However, the optical detector is so expensive that it causes the cost of the blood cell analyzer to be significantly high, which restricts the implementation of the detection technology for detecting displacement issues of the test tube rack.

SUMMARY

Therefore, a test tube rack of an analyzer pipeline, a shift detection method and a device using the same are provided.

A test tube rack of an analyzer pipeline that includes multiple test tube holders for containing test tubes is provided. The test tube rack of an analyzer pipeline includes a light blocker configured at a side wall of the test tube rack and across multiple test tube holders. A second feature area is on the light blocker between two adjacent test tube holders, a first feature area is between two adjacent second feature areas and a step gap with a predetermined depth is between the first feature area and a second feature area.

In one embodiment of the method for fusing at least one ultrasound image and a pre-acquired modality image of the present invention, multiple frames of ultrasound images are selected in the selecting step. The method further includes a breath model built step and a breath-correcting step. The breath model built step is for building a breath model according to the ultrasound video data. The breath-correcting step is conducted before the registering step or during the fusion step for implementing the breath model to correct the multiple frames of ultrasound images into the same breath depth level.

A shift detection method implemented by using the test tube rack includes acquiring a detection signal outputted from a sensor in a single shifting process of the test tube rack, a stop voltage from the detection signal when the single shifting process ends and a limit voltage from the detection signal during the single shifting process from the detection signal. Determining whether a ratio of the limit voltage and the stop voltage satisfies a first condition. If the first condition is satisfied, the single shifting process of the test tube rack is determined as correct; otherwise, the single shifting process of the test tube rack is determined to be false.

A detecting device using the test tube rack of the analyzer pipeline includes a voltage acquisition module and a shift determination module. The voltage acquisition module acquires a detection signal outputted from a sensor in a single shifting process of the test tube rack, a stop voltage from the detection signal at the end of the single shifting process and a limit voltage from the detection signal during the single shifting process. The shift determination module determines whether a ratio of the limit voltage and the stop voltage satisfies a first condition. If the first condition is satisfied, the single shifting process of the test tube rack is determined as correct; otherwise, the single shifting process of the test tube rack is determined as false.

An analyzer pipeline system includes: an analyzer; a test tube rack; a driving apparatus for driving the test tube rack; a sensor for detecting a first feature area and a second feature area in a shifting process of the test tube rack and outputting a detection signal correspondingly; and a processor including a detecting device for detecting the shift of the test tube rack. The detecting device, coupled to an output of the sensor, receives the detection signal outputted from the sensor to determine whether the shifting process of the test tube rack is correct.

The test tube rack only includes the first feature areas and the second feature areas for shift detection; the detecting area for the sensor avoids detecting the area of the test tubes so that the detection signals are not influenced by the reflected signals generated from the test tubes and tags. Therefore, no test tube would be lost for detection when the shifting process of the test tube is false so as to keep the reliability of the pipeline system.

The shift detection method disclosed in the present embodiment is a relative value signal detecting algorithm in a feature area. Under this algorithm, the sensitivity requirement for the implemented reflective optical sensor could be significant reduced. Basically, it could be satisfied by a general type reflective optical sensor so as to reduce the cost of reflective optical sensors.

BRIEF DESCRIPTION OF THE DRAWINGS

For explaining the embodiments of the present application or conventional technology more clearly, the figures used for explaining the embodiments or conventional background are introduced below. Obviously, in the drawings, similar drawings contain similar symbols for the same device or part, or for a part which has an analogous function and/or analogous structure. It should be understood that these drawings describe different kinds of embodiments, but are not to be considered as limitations of their scope.

DETAILED DESCRIPTION

Specific details for fully understanding each of embodiments and implemented by those skilled in the art are provided in the below description. However, it should be understood for those skilled in the art that the present invention is able to be implemented without the specific details as well. In some embodiments, conventional structures and functions are omitted to avoid confusion in the descriptions of the embodiments.

Unless it is acquired clearly under context of the descriptions, the terms “comprise” and “include” should be defined as an opening definition but not as a limited or an exhaustive definition.

Figure 1:
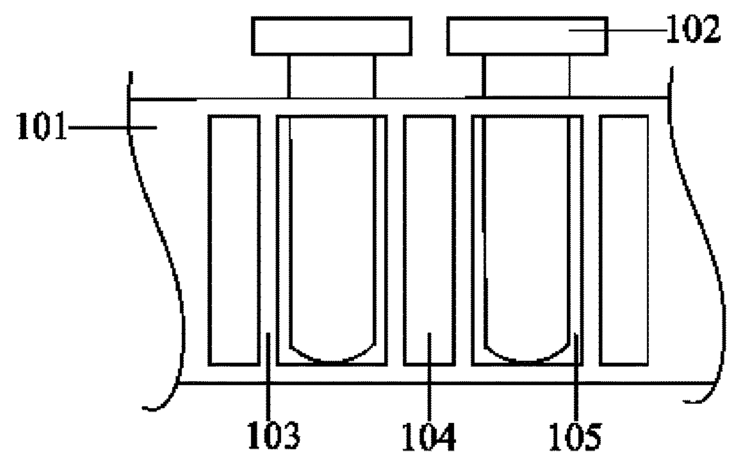
FIG. 1 is a structure schematic of a conventional test tube rack of an analyzer pipeline.
Figure 2:
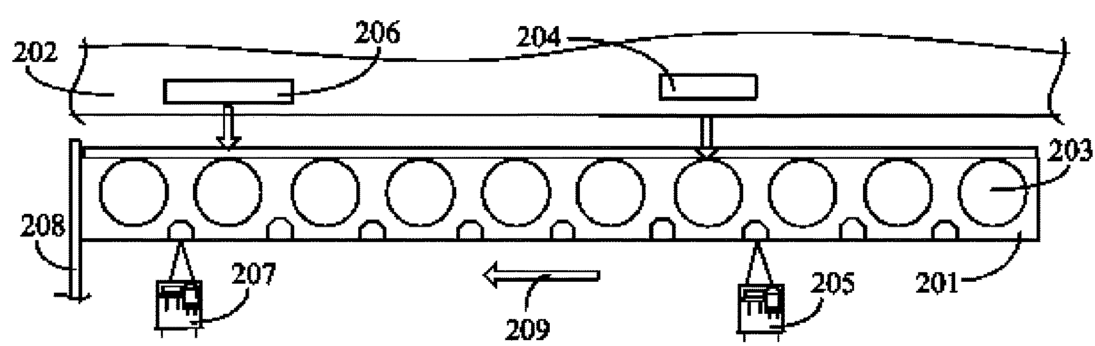
FIG. 2 is a working schematic of an analyzer pipeline with a test tube rack and shift detection device thereof for one embodiment of the present application.

FIG. 2 is a working schematic of an analyzer pipeline with a test tube rack and shift detection device thereof for one embodiment of the present application. The analyzer pipeline is able to include one or multiple analyzers, but only one analyzer is shown in FIG. 2. The present embodiment is also described under one analyzer structure. The above analyzer could be selected from a blood cell analyzer, a biochemistry analyzer or a smear machine. In the pipeline, a test tube rack 201 is transported to a detection area of an analyzer 202. A test tube 203 is shifted one test tube holder at a time to pass through a first sensor 205 located on a test tube detecting position 204 and through a second sensor 207 located on a sample collecting position 206 in sequence. Because a block apparatus 208 is implemented to block the test tube rack at a target position for each shifting step of the pipeline, the test tube rack cannot be shifted ahead but can only be left behind because of the lost steps of a motor, slip of a shifting belt or delay for pasting a tag. Therefore, the shift detection for the test tube rack needs to detect only whether the test tube rack is left behind in its predefined location, whether the backward distance is under allowable ranges and whether the test tube rack is shifted on the predefined location precisely. An arrow symbol 209 shown in FIG. 2 defines the shifting direction of the test tube rack.

Figure 3:
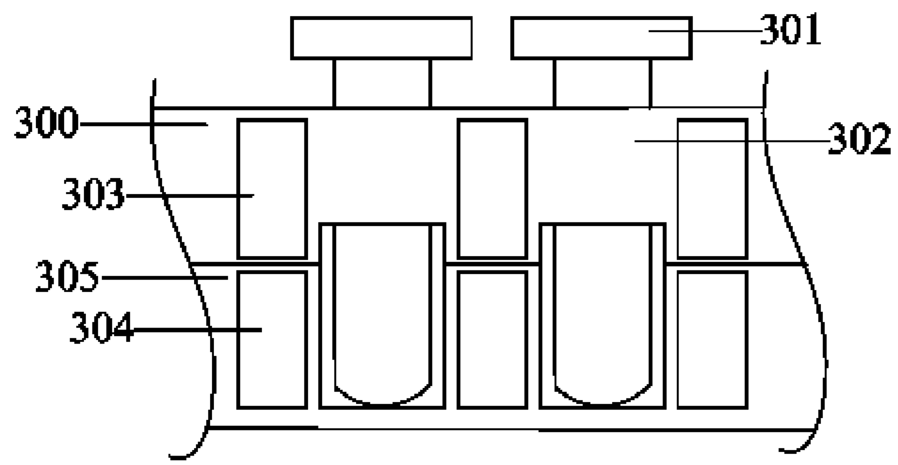
FIG. 3 is a structure schematic of a test tube rack for one embodiment of the present application.

Referring to FIG. 3, a plurality of test tube holders, which are able to carry a test tube 301, are configured at a test tube rack of a pipeline. A light blocker 300, which spans multiple test tube holders, is formed on one side of the test tube rack (such as the side of the rack facing the light sensor). A second feature area 303 is configured on the light blocker 300 between two adjacent test tube holders. A first feature area 302 is configured between two adjacent second feature areas 303. A step gap with a predetermined depth is formed between the first feature area 302 and the second feature area 303. The first feature area 302 and the second feature area 303 are configured on the light blocker 300 alternately and consistently.

In one embodiment, the second feature area 303 is a groove with a predetermined depth lower than the first feature area 302, or the second feature area 303 is a protrusion with a predetermined height higher than the first feature area 302. In the embodiment of the present application, for explaining but not restricting, the second feature area 303 is defined as a groove with a predetermined depth lower than the first feature area 302.

It should be noted that the first feature area 302 could be an area without any machining work. Actually, it could be the original side wall of the test tube rack. The step gap between the first feature area 302 and the second feature area 303 could be formed by machining the second feature area 303. For example, the second feature area 303 could be machined as a groove with a predetermined depth lower than the first feature area 302 or a protrusion with a predetermined height higher than the first feature area 302. Obviously, in another embodiment, it is also workable by machining the first feature area 302 to realize the step gap between the first feature area 302 and the second feature area 303. Alternatively, in some other embodiment, the first feature area 302 and the second feature area 303 could be machined as a groove and a protrusion individually, or instead, as a protrusion and a groove on the contrary.

In the embodiment, the second feature area 303 is selected as a groove with a predetermined depth lower than the first feature area 302. The predetermined depth of the groove is between 5 and 7 mm; more particularly, 6 mm could be selected. Under the above, the first feature area 302 is shaped as a protrusion correspondingly. It should be noted that the detection signal from the sensor should be a light beam when the sensor is implemented as a reflective optical sensor; a light beam has a cross-section which is defined as a facula (light spot). In general, the width of the first feature area 302 and the second feature area 303 should both be larger or at least equal to the facula of the light beam. However, in some other embodiments, the width of the first feature area 302 and the second feature area 303 could also be a little bit smaller than the facula of the light beam, but only under the condition that the reflected light from the first feature area 302 and the second feature area 303 still has distinguishable differences of strength. In the present embodiment, the width of the second feature area 303 is configured as 6 mm and the width of the first feature area 302 is referred to as the width of the test tube holder. In another embodiment, a sound sensor, such as an ultrasound sensor, could be implemented to detect the first feature area 302 and the second feature area 303 according to the strength of reflecting ultrasound waves.

The light blocker 300 could be selectively configured at the upper portion or the down portion of the side wall of the test tube. In the present invention, the light blocker 300 is configured at the upper portion of the side wall of the test tube to strengthen the stability of the test tube rack. Since many other parameters are needed to be detected by the analyzer in the analyzing process, a third feature area 304 is configured at a portion of the side wall which is not defined as the light blocker 300. The third feature area 304 is configured at two sides of the test tube holder, and is defined as a groove with a predetermined depth lower than the side wall of the test tube rack or a protrusion higher than the side wall of the test tube rack. The side wall of the test tube rack is the side of the rack pasted with the light blocker 300, shown as 305 in FIG. 3. On the other hand, the test tube holder is still maintained as a through hole with a rectangular shape front to back for implementing the detection of other parameters, such as scanning a tag on a test tube.

When the test tube rack of the present application is conducting a shift detection, the distance between the optical coupler and the first feature area 302 is approximately at the peak point of the reflecting signal strength by adjusting the position of the test tube rack to aim the focal point on the center of the groove (the second feature area 303). Every time the test tube rack is shifted, the sensor scans and aims on the center of the next groove after aiming on the center of the previous groove. Under the above, the distance between the reflecting surface of the reflected light and the sensor is recorded for containing a far-close-far change in the shifting process. Synchronously, the strength of the reflecting signal containing a high—low—high change is also recorded in the shifting process. In the present application, the depth of the test tube rack groove is 6 mm. For a general type reflective optical sensor, a 6 mm step gap would cause a not less than 50% change of signal strength for the reflected signal generated by the general type reflective optical sensor so as to ensure the accuracy of above sifting detection.

Figure 4:
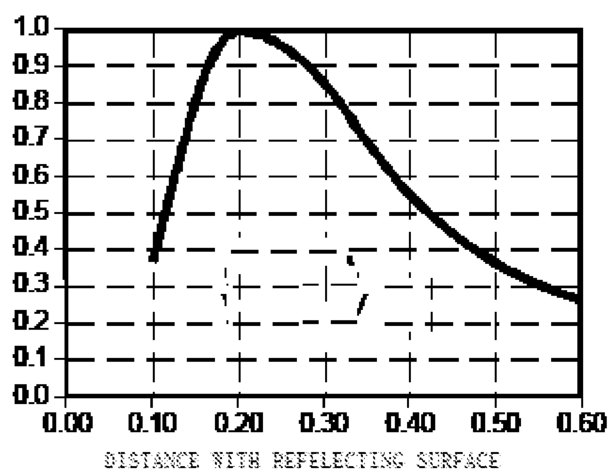
FIG. 4 is a diagram of a general type reflective sensor shown with a characteristic curve relating to its reflecting signal/distance relationship (distance sensitivity curve).

FIG. 4 is a diagram of a general type reflective optical sensor showing a characteristic curve relating to its reflecting signal/distance relationship (distance sensitivity curve). It is shown that when the distance between the reflecting surface and the sensor increases from 0.2 inch to 0.42 inch, the detected reflecting signal decays to 50% (1 inch equals). It is enough to provide an appropriate sensitivity for sensing reflected light under the above; therefore, different from conventional implementations, the requirements of the shift detection of the test tube rack are satisfied only by implementing a general type reflective optical sensor in the present application.

A 6 mm wide by 6 mm deep strip-shaped groove is configured between two adjacent test tube holders at the upper portion of the side wall of the test tube rack in the present application. A test tube holder 20 mm wide is configured between two adjacent grooves, and the upper portion of the test tube holder between two adjacent grooves 320 is the complete first feature area 302 (plate) but not a passing-through structure like the conventional one. Therefore, the whole structure of the upper side wall of the test tube rack in sequence is a continuous combination comprising a "the groove 303—the plate 302—the groove 303—the plate 302—the groove 303 . . . " structure. On the other hand, if the second feature area 303 is configured as a protrusion, the whole structure of the upper side wall of the test tube rack in sequence is a another continuous combination comprising a "the protrusion 303—the plate 302—the protrusion 303—the plate 302—the protrusion 303 . . . " structure. Since the test tube holder (the first feature area 302) is not a passing-through structure, the test tube 301 would not be detected by the sensor so that the reflecting signal would not be influenced by reflected light from the test tube 301 or the code tag pasted on it. Under the above implementation, the sensor could avoid a wrong determination for the shifting state of the test tube rack caused by false high-reflective signals.

Figure 5:
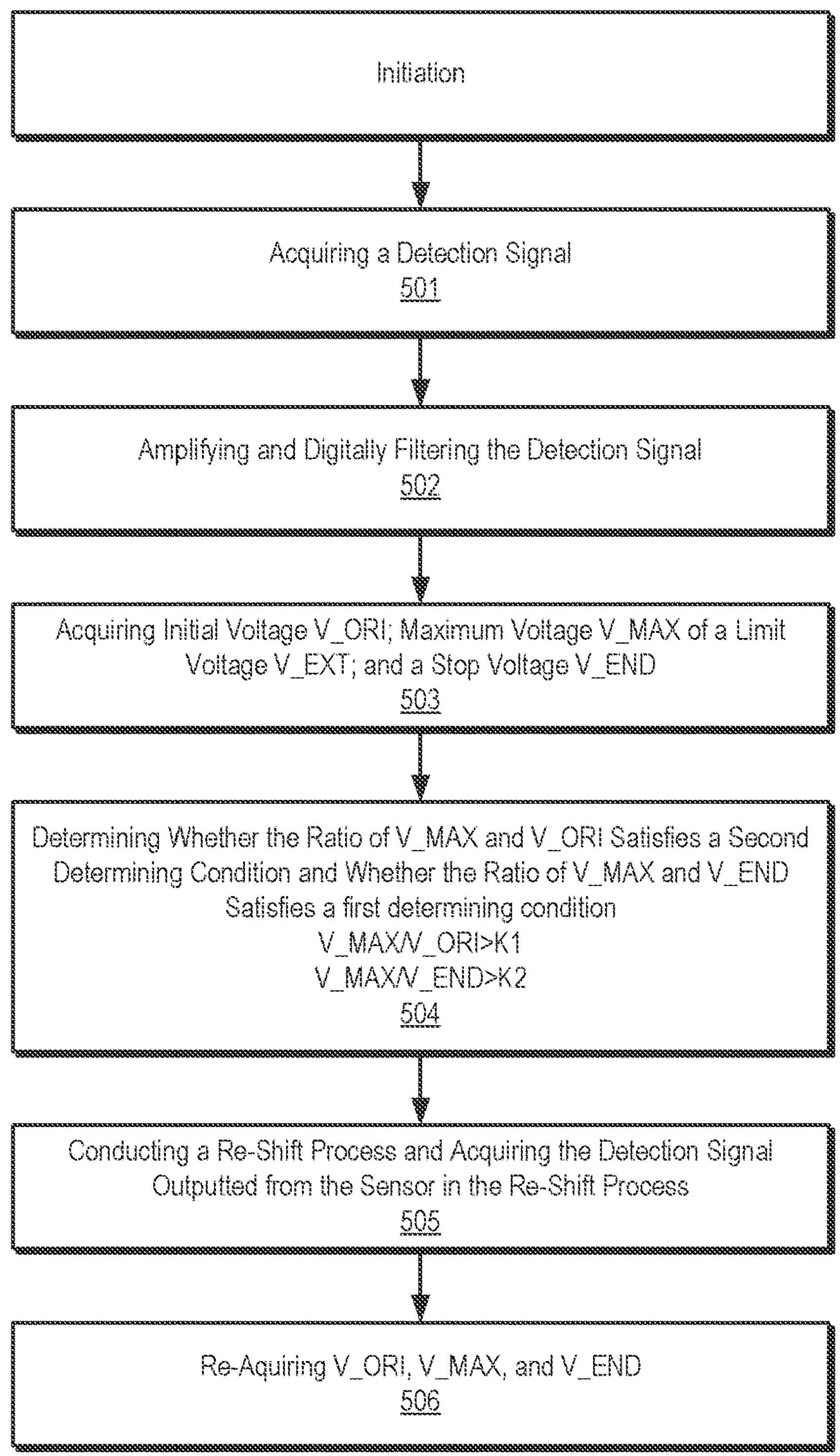
FIG. 5 is a process schematic of a shift detection method for a test tube rack applied in an analyzer pipeline of one embodiment of the present invention.

FIG. 5 discloses a process schematic of a shift detection method for a test tube rack applied in an analyzer pipeline of one embodiment of the present invention, which comprises:

STEP 501: acquiring a detection signal inputted from a sensor from a single step shifting process of a test tube rack. The single step shifting is defined as the step from when the test rack tube starts its shift to when the shift is stopped.

STEP 502: amplifying and digital filtering the detection signal to remove error influences caused from noises or an uneven surface of the test tube rack. In the present embodiment, a middle value filtering algorithm is selected to implement the above process.

STEP 503: an initial voltage V_ORI, defined as the voltage value detected when the test tube rack starts to shift; a stop voltage V_END, defined as the voltage value detected when the test tube rack ends its shift; and a limit voltage V_EXT, defined as the maximum absolute value of voltage from the beginning to the end of the shift of the rack, are acquired from the detection signal after the digital filtering process in STEP 502.

It should be noted that when the second feature area is configured as a groove, the value of the detection signal should correspondingly become " . . . low—high—low—high—low . . . " and the limit voltage V_EXT should be detected as a maximum voltage V_MAX. On the contrary, when the second feature area is configured as a protrusion, the value of the detection signal should correspondingly become " . . . high—low—high—low—high . . . " and the limit voltage V_EXT should be detected as a minimum voltage V_MIN. In the present embodiment, for explaining but not restricting, the limit voltage V_EXT is selected as the maximum voltage V_MAX by configuring the second feature area as a groove.

Figure 6:
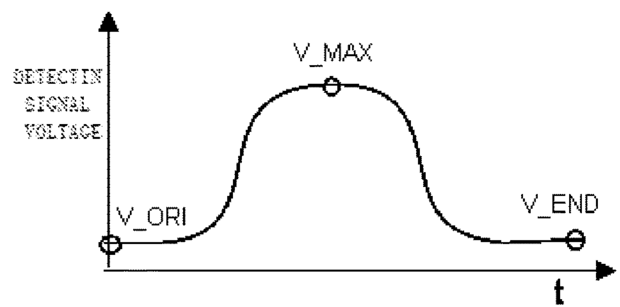
FIG. 6 is a schematic of a detection signal recording all changes in one single shifting process for a test tube rack.

FIG. 6 shows a schematic of a detection signal recording all changes in one single shifting process for a test tube rack. Firstly, the initial voltage V_ORI is detected when the test tube rack starts to shift and defines the position of V_ORI as a starting point; after that, the stop voltage V_END is detected when the test tube rack ends its shift and defines the position of V_END as an ending point. Since the groove—plate—groove structure of the test tube rack is shifted through the sensor in sequence, the detection signal from the sensor would correspondingly represent as a bell-shaped curve; the maximum voltage V_MAX is acquired between the starting point and the ending point. When the second feature area of the test tube rack is configured as a protrusion, the detection signal from the sensor would correspondingly represent as an upside-down bell-shaped curve; the minimum voltage V_MIN is acquired between the starting point and the ending point.

STEP 504: determining whether the ratio of V_MAX and V_ORI satisfies a second determining condition and whether the ratio of V_MAX and V_END satisfies a first determining condition. If the first determining condition and the second determining condition are both satisfied, the shifting state of the test tube rack is determined as correct. Otherwise, the shifting state of the test tube rack is determined as false. It should be understood that, in other applications, by merely determining whether the ratio of V_MAX and V_END satisfies the first determining condition, the shifting state of the test tube rack could also be determined. When the ratio of V_MAX and V_END satisfies the first determining condition, it is determined that the shifting state of the test tube rack is correct. If the first determining condition is not satisfied, the shifting state of the test tube rack is determined as false. In the present embodiment, for making sure the accuracy of the shifting state determination, the judgment of the ratio of V_MAX and V_ORI is further implemented.

In the present embodiment, the first determining condition is defined as the ratio of V_MAX and V_END is larger than a first factor k1, and the second determining condition is defined as the ratio of V_MAX and V_ORI is larger than a second factor k2, which are shown as the below functions:

$$V\_MAX/V\_END>k1 \quad \text{function (1)}$$

$$V\_MAX/V\_ORI>k2 \quad \text{function (2)}$$

In the present embodiment, k1 and k2 are both a constant number larger than 1. Decisions about how to get a suitable value for k1 and k2 relate to the relative difference between the detection signal of the plate of the test tube rack and the detection signal of the groove of the test tube rack. When the relative difference is larger, k1 and k2 are increased correspondingly. The relative difference, under the above disclosures, relates to characteristic factors such as the reflecting signal —distance feature or the depth of the groove. In one embodiment, for general type reflective optical sensors, k1 and k2 are defined as a value 1.5-2.0 under the condition that the depth of the test tube rack groove is defined as 6 mm. Usually, k1 and k2 could be selected as the same value.

In another embodiment, when the second feature area is defined as a protrusion, the first determining condition is defined as the ratio of V_MIN and V_END is smaller than a third factor k3, and the second determining condition is defined as the ratio of V_MIN and V_ORI is smaller than a fourth factor k4, which are shown as the below functions:

$$V\_MIN/V\_END<k3 \quad \text{function (3)}$$

$$V\_MIN/V\_ORI<k4 \quad \text{function (4)}$$

Wherein k3 and k4 are constants whose values are both between 0 and 1, decisions about how to get a suitable value for k3 and k4 are similar to those of k1 and k2, so those factors are omitted for clarity of the descriptions thereof.

In a single shifting process, when function (1) and function (2) are both found, it means that V_ORI is corresponding to a groove area of the test tube rack, V_END is corresponding to the next groove area of the test tube rack and V_MAX is corresponding to the plate area of the test tube rack. The above changes prove the shifting process of the test tube rack is passed through a groove—plate—groove process and the test tube rack is definitely shifted to a right locating position. In the other words, the shifting state of the test tube rack is defined as correct under the above. If the function V_MAX/V_END>k1 is not found, it means the previous groove of the rack has left the sensing area of the sensor but the next groove of the rack is not shifted to the same sensing area in sequence, which explains why the present plate area of the rack stayed at the sensing area of the sensor. In other words, the shifting state of the test tube rack is defined as false under the above. If the function V_MAX/V_ORI>k2 is not found, it means the test tube rack was stuck at the pipeline and the previous plate area of the rack stayed at the sensing area of the sensor. Usually, when a false state of the shifting process happens, a correction step would be conducted before restarting the next shifting process. Therefore, function (2) is basically sustained under normal situations.

STEP 505: controlling the test tube rack for conducting a re-shift process, and acquiring the detection signal outputted from the sensor in the re-shift process. The re-shift process is defined as an additional shifting process which controls the test tube rack to be shifted again to relocate the test tube rack at the right locating position when the shifting process of the test tube rack is determined as false at present. It should be noted that the driving mechanism controlling the shifting process of the test tube rack is normally implemented by a stepper motor. A stepper motor is capable of moving at a specific step length which equals the distance of a single shift of the test tube rack. In the re-shift process, the shifting distance is obviously smaller than the step length of the stepper motor. It means the stepper motor can drive the test tube rack to shift only its original step length. However, since a blocker mechanism is implemented just at the right locating position, the blocker would block the test tube rack to stay at the right locating position so that the over-shifting situation of the test tube rack has no chance to happen under the above implementation.

STEP 506: considering the detection signal of the previous shifting process with the detection signal of the re-shift process to re-acquire the initial voltage, the stop voltage and the maximum voltage, and re-conducting STEP 504 again. In another embodiment, if only V_END voltage is acquired for determining whether the shifting process of the test tube rack is false in STEP 503, correspondingly, an implementation in which only V_END voltage is re-acquired after the re-shift process is conducted is also workable.

In one embodiment, details for implemented STEP 505 and STEP 506 are disclosed as below: Buffering the two feature signals V_ORI voltage and V_MAX voltage and re-shifting the test tube rack to acquire three feature signals during the re-shifting process, which are V_ORI, V_MAX and V_END. After the above, comparing the V_ORI voltage buffered in the pipeline system with the V_ORI voltage acquired during the re-shifting process to choose the one with lower voltage then renew V_ORI as the lower value. After that, comparing the V_MAX voltage buffered in the pipeline system with the V_MAX voltage acquired during the re-shifting process to choose the one with higher voltage then renew V_MAX as the higher value. After that, implementing the renewing V_ORI, renewing V_MAX and V_END acquired during the re-shifting process to conduct the determination of function (1) and function (2). If the determination of function (1) and function (2) is satisfied, it proves the test tube rack reaches the right locating position at the end. If the determination of function (1) and function (2) is not satisfied, it means the re-shifting process is false and the test tube rack does not reach the right locating position still. Another implementation for acquiring the renewing V_ORI, renewing V_MAX and V_END acquired during the re-shifting process is disclosed below: saving the whole detection signal (the wave curve) from the beginning point to the ending point, and mapping all the curve of above with the detection signal (the wave curve) acquired during the re-shifting process to find the three feature points V_ORI, V_MAX and V_EDN.

Normally, the step of buffering data does not exist in the disclosed shift detection method of the test tube rack. Acquired data in the previous step would be replaced by the new data acquired at the next process. However, in the present application, the buffering step is implemented in the shift detection method of the test tube rack. Therefore, the feature voltages or the whole detection signal acquired in the shifting process could be saved respectively to conduct the re-shifting process.

It should be noted that the re-shifting can be conducted for only one time or for multiple times until the renewing V_ORI, V_MAX and V_END satisfy with the determination condition since that shows the test tube rack has shifted to the right locating position.

Figure 7:
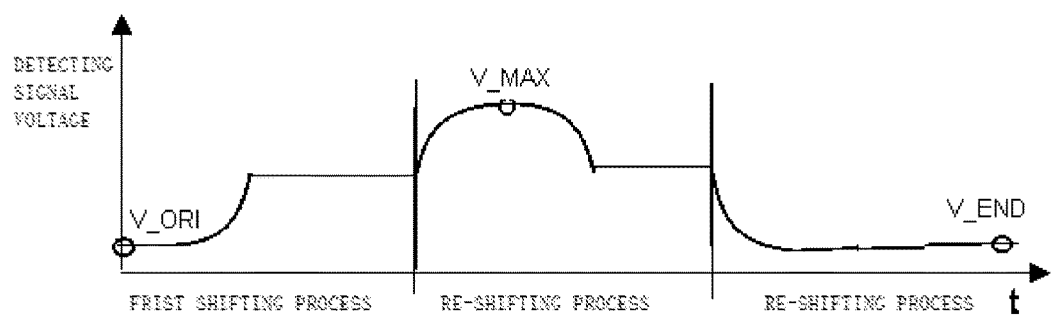
FIG. 7 is a schematic of a detection signal recording all changes in one single re-shifting process for a test tube rack.

FIG. 7 shows a schematic of a detection signal recording all changes in one single re-shift process for a test tube rack in a detailed embodiment. The test tube rack is stuck at some specific position corresponding to a signal rising edge and the corresponding V_MAX equals the V_END under the above situation, which is not satisfied with the function of V_MAX/V_END>k1, so that a re-shifting process is initiated automatically. The peak point of the detection signal is detected at the first re-shifting process, which means the plate area of the rack reaches the right locating position, but the V_END is still too high, which means the test tube rack is still stuck at some specific position corresponding to some signal falling edge, to fail the determining condition. Therefore, a second re-shifting process is conducted accordingly. In the second re-shifting process, the V_END value corresponding to the groove area of the test tube rack is detected, which means the test tube rack is shifted to the right locating position, and V_MAX is still holding on the peak value acquired at the first re-shifting process so that the determining condition is satisfied. It is understood, by comparing FIG. 6 with FIG. 7, that although multiple re-shifting processes are conducted, the detected maximum voltage, the beginning voltage and the ending voltage are respectively the same as the corresponding values detected when the determining condition is satisfied at a single shifting process. It means, for the implementation disclosed in the present application, key features of the detection signal would not be lost, and key features of detected signals acquired at the re-shifting process are the same as detected signals acquired when the determining condition is satisfied at a single shifting process. Therefore, the whole shifting process disclosed in the present embodiments supports high reliability and the issue of false negative detection is avoidable accordingly.

The shift detection method disclosed in the present embodiment is a relative value signal detecting algorithm in a feature area. Under this algorithm, the sensitivity requirement for the implemented reflective optical sensor could be significantly reduced. Basically, it could be satisfied by a general type reflective optical sensor so as to reduce the cost of reflective optical sensors.

In a conventional shift detection method of the test tube rack, it can only stop the pipeline and raise a warning when the test tube rack is not shifted to the right locating position at the first time in the shifting process. The pipeline system does not automatically re-conduct one or multiple re-shifting processes to exclude faults, which is not intelligent and could cause inconvenience for the user. A re-shifting process is embodied in the present embodiment, which means a recovering detection algorithm for a breakdown point of the pipeline system is implemented. When the test tube rack is not shifted to the right locating position at the first time shifting process, it is possible to automatically re-shift the test tube rack through the above breakdown point recovering algorithm until the test tube rack is shifted to the right locating position. The above embodiment is significantly more intelligent, so the user experience is accordingly better. Those skilled in the art will understand that, excepting the technical solutions disclosed in the present embodiment, other detection solutions could be implemented alternatively, such as the conventional absolute value detection solution.

Figure 8:
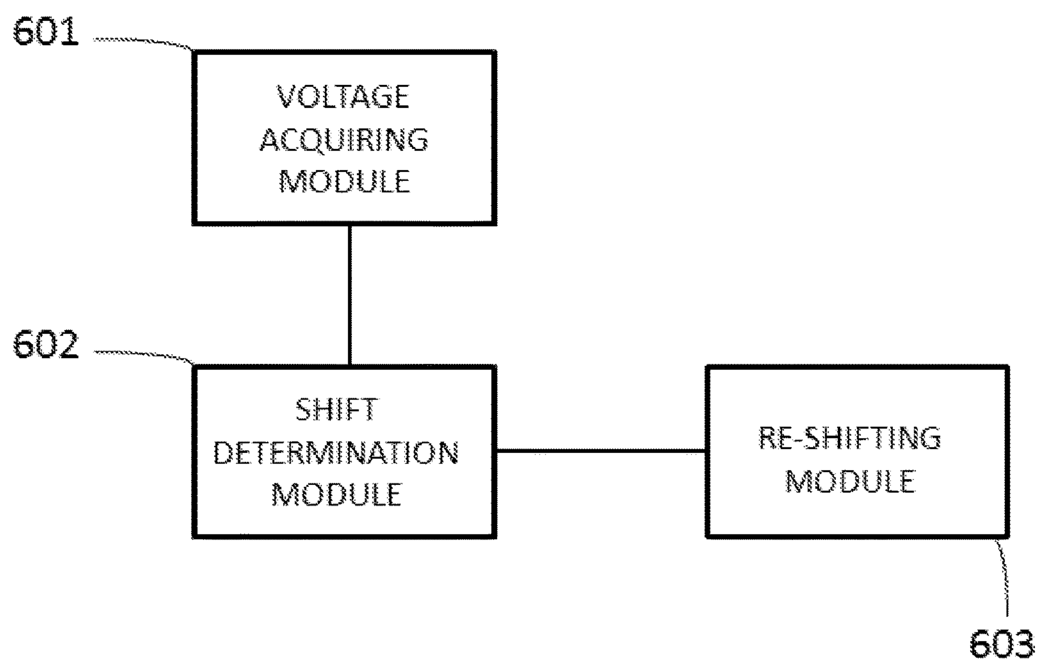
FIG. 8 is a module schematic of a shift detection device of the test tube rack for one embodiment of the present application.

FIG. 8 shows a module schematic of a shift detection device of the test tube rack for one embodiment of the present application. In the present embodiment, the detection device for shift detection of the test tube rack comprises a feature voltage acquisition module 601 and a shifting determination module 602.

The feature voltage acquisition module 601 is implemented for acquiring the detection signal outputted from the sensor in the single time shifting process of the test tube rack. The feature voltage acquisition module 601 acquires the initial voltage when the test tube rack starts to be shifted, the stop voltage when the test tube rack ends its shift and the limit voltage among the shifting process of the test tube rack.

The shifting determination module 602 is implemented to determine whether the first determining condition is satisfied by the ratio between the limit voltage and the end voltage. If it is satisfied, the test tube rack is shifted to the proper locating position. If it is not satisfied, the test tube rack has failed to shift to the correct location, or right locating position.

In the present embodiment, the feature voltage acquisition module 601 further acquires the initial voltage when the test tube rack starts to be shifted in the single shifting process of the test tube rack after the detection signal outputted from the sensor in the single time shifting process is acquired. The shifting determination module 602 determines whether the second determining condition is satisfied by the ratio between the limit voltage and the initial voltage for the first determining condition to be determined. If both the first determining condition and the second determining condition are satisfied, the test tube rack is shifted to the right locating position. Otherwise, the determination of the shifting process of the test tube rack is false.

In the present embodiment, the first determination condition is defined as whether the ratio between the limit voltage and the stop or end voltage is larger than the first factor, and the second determination condition is defined as whether the ratio between the limit voltage and the initial voltage is larger than the second factor. In another embodiment, the first determination condition is defined as whether the ratio between the limit voltage and the stop voltage is smaller than the first factor, and the second determination condition is defined as whether the ratio between the limit voltage and the initial voltage is smaller than the second factor.

In one embodiment, the shifting determination module 602 is able to control the warning device to initiate a warning when the shifting determination module 602 detects the shifting process of the test tube rack has failed.

In the present embodiment, the detection device for shift detection of the test tube rack comprises a re-shifting module 603. The re-shifting module 603 is implemented to control the re-shifting process of the test tube rack after the shifting determination module 602 detects the shifting process of the test tube rack has failed and to acquire the detection signals outputted from the sensor during the re-shifting process to renew the limit voltage, the stop voltage and the initial voltage by comparing the detection signal acquired at the previous shifting process. After the above, the shifting determination module 602 determines whether the ratio between the renewing limit voltage and the renewing stop voltage satisfies the first determining condition, and whether the ratio between the renewing limit voltage and the renewing initial voltage satisfies the second determining condition. If both the first determining condition and the second determining condition are satisfied, it is determined that the shifting of the test tube rack is correct. Otherwise, the re-shifting module 603 is controlled to conduct the re-shifting process until the shifting of the test tube rack is correct. It should be noted that, if the determination of whether the ratio between the limit voltage and the stop voltage satisfies the first determining condition conducted in the previous shifting process, only the limit voltage and the stop voltage should be renewed during the re-shifting process of the test tube rack.

In the present application, details about how the re-shifting module 603 re-shifts the test tube rack and re-acquires the initial voltage, the stop voltage and the limit voltage are described as below:

During the re-shifting process, the initial voltage, the stop voltage and the limit voltage are acquired from the detection signal outputted from the sensor. The above voltages are compared with the initial voltage, the stop voltage and the limit voltage from the detection signal outputted from the sensor buffered in the previous shifting process. The smaller of the above two initial voltages is selected as a present initial voltage. The larger of the above two limit voltages is selected as a present limit voltage when one of above two limit voltages is at its peak value. Alternatively, the smaller one of above two limit voltages is selected as a present minimum value voltage when one of above two limit voltages is at its minimum value. The stop voltage acquired at the re-shifting process is selected as a present end voltage. In another embodiment, the re-shifting model 603 integrates detection signals outputted from the sensor in multiple re-shifting processes as a complete detection signal, and the present initial voltage, the limit voltage and the present stop voltage are selected from the complete detection signal.

The shift detection method disclosed in the present embodiment is a relative value signal detecting algorithm in a feature area. Under this algorithm, the sensitivity requirement for the implemented reflective optical sensor could be significantly reduced. Basically, it could be satisfied by a general type reflective optical sensor so as to reduce the cost of reflective optical sensors.

The analyzer pipeline system in one embodiment includes one or multiple analyzers, the test tube rack provided in the above embodiment, a driving mechanism for driving the shift of the test tube rack, a sensor for detecting the first feature area and the second feature area in the shifting process of the test tube rack and outputting the corresponding detection signals, and a processor, the processor including a detecting device for detecting the shift of the test tube rack, the detecting device, coupled to the output terminal of the sensor, receiving the detection signals outputted from the sensor to determine whether the test tube rack is shifted to the right locating position.

In one embodiment, the detecting device acquires the initial voltage at the beginning of a single shift process of the test tube rack according to the detection signals outputted in accordance with the first feature area and the second feature area. The detecting device further acquires the stop voltage at the end of the shifting process and the limit voltage between the beginning and the end of the shifting process. After that, the detecting device determines whether the ratio of the limit voltage and the stop voltage satisfies the first determining condition and whether the ratio of the limit voltage and the initial voltage satisfies the second determining condition. If both conditions are satisfied, the shifting process of the test tube rack is determined as correct; otherwise, it is determined as false.

The detecting device is also implemented for controlling the re-shifting process of the test tube rack if the shifting process of the test tube rack is determined as false. The detecting device further acquires the detection signals outputted from the sensor during the re-shifting process to combine the above with the detection signals acquired in the previous shifting process to regain the initial voltage, the stop voltage and the limit voltage. If the ratio of the limit voltage and the stop voltage satisfies the first determining condition and the ratio of the limit voltage and the initial voltage satisfies the second determining condition, the test tube rack is determined as shifting to the right locating position. Otherwise, the re-shifting process of the test tube rack is conducted again until the test tube rack is shifted to the right locating position.

Referring to FIG. 2, in the present embodiment, the sensor includes the first sensor 205 and the second sensor 207 and the first sensor 205 is configured at the test tube detecting position 204 and the second sensor 207 is configured at the sample collecting position 206. In the present embodiment, the first sensor 205 and the second sensor 207 are implemented by two identical reflective optical sensors. The first sensor 205 is used to confirm whether the test tube rack is shifted to the test tube detecting position 204 since a wrong shift of the test tube 203 could cause wrong tag-numbering of the test tube 203 (sample). The second detector 207 is configured at the sample collecting position 206. A wrong shift at the sample collecting position 206 could cause mis-collection of samples. In general, the test tube rack has 10 test tube holders. There are six intervals of test tube holders between the first sensor 205 and the second sensor 207. In some other embodiments, interval numbers between the first sensor 205 and the second sensor 207 could be configured under detailed requirements. Since six intervals are configured between the first sensor 205 and the second sensor 207 and there are 10 test tube holders for a test tube rack, the test tube rack could be detected by the above two detectors at the same time when the test tube rack is shifted to certain positions. In the above situation, the pipeline system is workable to take detection results only from a fixing detector selected from the above two. The reason to configure two detectors in some embodiments is to make sure that the shift detection can be conducted for all the test tubes at any time when test tube detection and sample collection are conducted on all the test tubes.

Of course, in some embodiments, one detector could be implemented for shift detection, but for making sure that shift detection can be conducted for all the test tubes at any time when test tube detection and sample collection are conducted on all the test tubes, the test tube rack should be extended at certain portions. The same feature areas are configured on the extended portion of the test tube rack for shift detection of the test tube rack. To implement the above configuration, the length of the test tube rack would be extended, which does not meet the requirements in reality. Therefore, the configuration with two detectors is selected in the present embodiment.

Figure 9:
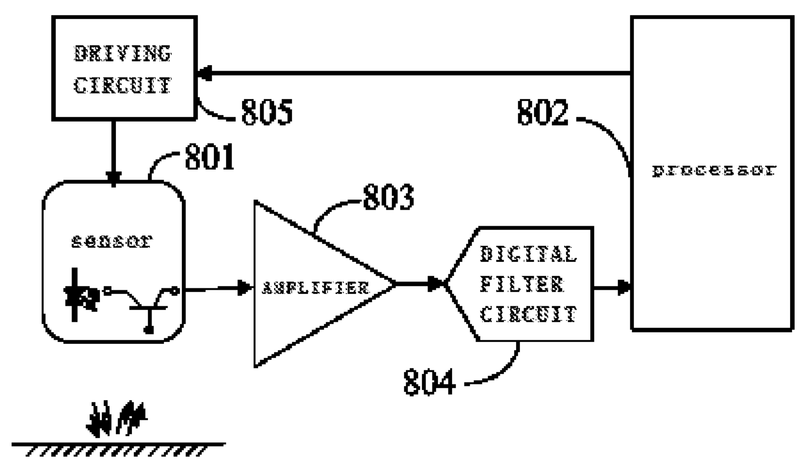
FIG. 9 is a partial detail circuit diagram of a shift detection device of the test tube rack for one embodiment of the present application.

FIG. 9 shows a partial detail circuit diagram of a shift detection device of the test tube rack for one embodiment of the present application. An amplifier circuit 803 and a digital filter 804 are configured between a sensor 801 and a processing circuit 802 for amplifying the detection signals outputted from the sensor 801 and conducting a digital filtering for the amplified signals. The processing circuit 802 acquires the initial voltage, the stop voltage and the limit voltage from the digitally filtered signals. A driving circuit 805 is configured between the sensor 801 and the processing circuit 802 for driving the sensor 801 to emit detection signals. In the present embodiment, the processing circuit 802 is also capable of raising a warning (not shown) when the shifting process of the test tube rack is detected as false.

In one embodiment of the analyzer pipeline system, the test tube rack thereof, the shift detection method and the device using the same, firstly, the test tube rack only includes the first feature areas and the second feature areas for shift detection; the detecting area for the sensor avoids detecting the area of the test tubes so that the detection signals are not influenced by the reflective signals generated from the test tubes and tags. Therefore, no test tube would be lost for detection when the shifting process of the test tube is false so as to raise the reliability of this pipeline system. Secondly, a relative value signal detecting algorithm in a feature area is implemented as the shift detection method disclosed in the present embodiment. The relative value signal detecting algorithm determines the shift of the test tube rack through detecting the relative multiple numbers between the peak part and the weak part of the detection signals. Therefore, sensitivity requirements for the implemented reflective optical sensor could be significant reduced. Sensitivity requirements could be satisfied by a general type reflective optical sensor so as to reduce the cost of reflective optical sensors. Finally, when the test tube rack is not shifted to the right locating position at the first time shifting process, it is possible to automatically re-shift the test tube rack through the above breakdown point recovering algorithm until the test tube rack is shifted to the right locating position. Since the time interval for previous shifting to the re-shifting process is quite short, the user would not notice the analyzer had ever broken down. The above embodiment is significantly more intelligent, so that the user experience is accordingly better.

It is understandable for those skilled in the art that all or some of the processes disclosed in the embodiments of the present application are able to be implemented by instructing related hardware through computer programs. The above programs are able to be stored in the readable storage media of a computer. The above programs are able to include the implementation of all flow charts for all methods disclosed in the above embodiments in execution. The readable storage media include but are not limited to: hard disc, optical disc, read-only memory (ROM) and random access memory (RAM).

Although the present disclosure has been described through specific embodiments, the present disclosure is not limited to the specific embodiments described above. Those of skill in the art should understand that various modifications, alternatives and variations may be made based on the present disclosure, which all should be within the scope of protection of the present disclosure. Furthermore, "an embodiment" or "another embodiment" mentioned above may represent different embodiments, or may also be combined completely or partly in one embodiment.

The invention claimed is:

1. A detecting device for shift detection, comprising:

a test tube rack including a plurality of test tube holders for holding test tubes;

a drive component for driving the test tube rack;

a light blocker arranged on a surface of the test tube rack, the light blocker comprising a first feature area and a second feature area alternated with the first feature area, the first feature area and the second feature area optically blocking the test tubes, the second feature area having a depth different from the first feature area in a direction perpendicular to the surface of the test tube rack;

a reflective optical sensor for detecting a reflected signal from the first feature area and the second feature area of the light blocker to output a detection signal during a shifting process of the test tube rack by the drive component, a single test tube is shifted during the shifting process of the test tube rack;

a processor configured to acquire a stop voltage from the detection signal and a limit voltage from the detection signal during the shifting process, wherein the stop voltage is detected upon the test tube rack ending the shift, and the limit voltage is the maximum absolute value of voltage from the beginning to the end of the shift of the test tube rack; and the processor is further configured to determine whether a ratio of the limit voltage and the stop voltage satisfies a first condition; upon the determination that the first condition is satisfied, the shifting process of the test tube rack is determined as correct; otherwise, the shifting process of the test tube rack is determined as false.

2. The detecting device of claim 1, wherein the processor further acquires an initial voltage from the detection signal at the beginning of the shifting process of the test tube rack after the detection signal outputted from the sensor during the shifting process of the test tube rack is acquired; and further determines whether the ratio of the limit voltage and the stop voltage satisfies a first condition and also determines whether the ratio of the limit voltage and the initial voltage satisfies a second condition; if the first and second conditions are satisfied, the shifting process of the test tube rack is determined as correct; otherwise, the shifting process of the test tube rack is determined as false.

3. The detecting device of claim 2, wherein: the first condition is the ratio of the limit voltage and the stop voltage is larger than a first factor and the second condition is the ratio of the limit voltage and the initial voltage is larger than a second factor; or the first condition is the ratio of the limit voltage and the stop voltage is smaller than a first factor and the second condition is the ratio of the limit voltage and the initial voltage is smaller than a second factor.

4. The detecting device of claim 1, wherein the processor further controls an output device to outputs a warning signal when the shifting process of the test tube rack is determined as false, or further controls the driving component to drive the test tube rack to conduct a re-shifting process after the shifting process of the test tube rack is determined as false, acquires a second detection signal outputted from the sensor during the re-shifting process and re-acquires an initial voltage, a stop voltage and a limit voltage for the re-shifting process by comparing the second detection signal acquired in a previous shifting process with the second detection signal acquired during the re-shifting process; wherein the processor further determines whether the ratio of the re-acquired limit voltage and the re-acquired stop voltage satisfies the first condition; if the first condition is satisfied, the re-shifting process of the test tube rack is determined as correct; otherwise, the processor further controls the test tube rack to repeat the re-shifting process until the re-shifting process of the test tube rack is determined as correct.

5. The detecting device of claim 2, wherein the processor further controls the output device to outputs a warning signal when the shifting process of the test tube rack is determined as false, or further controls the driving component to drive the test tube rack to conduct a re-shifting process after the shifting process of the test tube rack is determined as false, acquires a second detection signal outputted from the sensor during the re-shifting process and re-acquiring an initial voltage, a stop voltage and a limit voltage for the re-shifting process by comparing the second detection signal acquired in a previous shifting process with the second detection signal acquired during the re-shifting process; wherein the processor further determines whether the ratio of the re-acquired limit voltage and the re-acquired stop voltage satisfies the first condition and whether the ratio of the re-acquired limit voltage and the re-acquired initial voltage satisfies the second condition; if the first and the second conditions are satisfied, the re-shifting process of the test tube rack is determined as correct; otherwise, the processor further controls the test tube rack to repeat the re-shifting process until the re-shifting process of the test tube rack is determined as correct.

6. The detecting device of claim 4, wherein the processor re-acquiring an initial voltage, a stop voltage and a limit voltage for the re-shifting process comprises: acquiring the initial voltage, the stop voltage and the limit voltage from the second detection signal outputted from the sensor; comparing the initial voltage, the stop voltage and the limit voltage for the re-shifting process with the initial voltage, the stop voltage and the limit voltage acquired from a detection signal buffered in the previous shifting process; selecting a smaller one from the above two initial voltages as a present initial voltage; selecting a larger one from the above two limit voltages as a present limit voltage when the two limit voltages are maximum voltages, or selecting a smaller one from above two limit voltages as a present limit voltage when the two limit voltages are minimum voltages; selecting the re-acquired stop voltage acquired in the re-shifting process as a present end voltage; or integrating detection signals outputted from the sensor in several shifting processes in sequence to generate an integrated detection signal; and acquiring the initial voltage, the stop voltage and the limit voltage from the integrated detection signal.

7. The detecting device of claim 1, further comprising a driving circuit between the sensor and the processor for driving the sensor to emit the detection signal.

8. The detecting device of claim 1, further comprising an amplifier between the sensor and the processor to generate an amplified detection signal.

9. The detecting device of claim 8, further comprising a digital filter between the amplifier and the processor to generate a filtered detection signal from the amplified detection signal.

10. The detecting device of claim 1, wherein the driving component comprises a step motor.

* * * * *